(12) United States Patent
Fan et al.

(10) Patent No.: US 7,005,265 B1
(45) Date of Patent: Feb. 28, 2006

(54) NONENZYMATIC CATALYTIC SIGNAL AMPLIFICATION FOR NUCLEIC ACID HYBRIDIZATION ASSAYS

(76) Inventors: Wenhong Fan, 1033 Crestview Dr., Apt. 311, Mountain View, CA (US) 94040; Alan M. Cassell, 1179 Minnesota Ave., San Jose, CA (US) 95125; Jie Han, 7703 Oak Meadow Ct., Cupertino, CA (US) 95014

( * ) Notice: Subject to any disclaimer, the term of this patent is extended or adjusted under 35 U.S.C. 154(b) by 482 days.

(21) Appl. No.: 10/178,683

(22) Filed: Jun. 20, 2002

(51) Int. Cl.
C12Q 1/68 (2006.01)
C07H 21/04 (2006.01)

(52) U.S. Cl. ............... 435/6; 435/287.2; 536/24.3
(58) Field of Classification Search ............... 435/6, 435/287.2; 536/24.3
See application file for complete search history.

(56) References Cited

U.S. PATENT DOCUMENTS

| | | | |
|---|---|---|---|
| 4,766,062 | A | 8/1988 | Diamond et al. |
| 4,766,064 | A | 8/1988 | Williams et al. |
| 4,795,701 | A | 1/1989 | Vary |
| 4,818,680 | A | 4/1989 | Collins et al. |
| 5,268,266 | A | 12/1993 | Fritsch et al. |
| 5,445,933 | A | 8/1995 | Eadie et al. |
| 5,888,780 | A | 3/1999 | Dahlberg et al. |
| 5,925,517 | A | 7/1999 | Tyagi et al. |
| 5,958,681 | A | 9/1999 | Wetmur et al. |
| 5,985,557 | A | 11/1999 | Prudent et al. |
| 5,994,069 | A | 11/1999 | Hall et al. |
| 6,001,567 | A | 12/1999 | Brow et al. |
| 6,043,060 | A | 3/2000 | Imanishi |
| 6,090,543 | A | 7/2000 | Prudent et al. |
| 6,103,476 | A | 8/2000 | Tyagi et al. |
| 6,130,047 | A | 10/2000 | Nadeau et al. |
| 6,238,927 | B1 | 5/2001 | Abrams et al. |
| 6,255,051 | B1 | 7/2001 | Hammond et al. |
| 6,268,490 | B1 | 7/2001 | Imanishi et al. |
| 6,358,685 | B1 | 3/2002 | Wetmur et al. |
| 6,361,945 | B1 | 3/2002 | Becker et al. |
| 6,531,302 | B1 * | 3/2003 | Nerenberg et al. .......... 435/91.2 |
| 2002/0045182 | A1 * | 4/2002 | Singh et al. .................. 435/6 |

FOREIGN PATENT DOCUMENTS

| | | |
|---|---|---|
| EP | 0 164 876 A1 | 12/1985 |
| EP | 0 167 238 A1 | 1/1986 |
| WO | WO 98/39352 | 9/1998 |
| WO | WO 98/53311 | 11/1998 |
| WO | WO 99/14226 | 3/1999 |
| WO | WO 00/56748 | 9/2000 |
| WO | WO 00/62036 | 10/2000 |
| WO | WO 00/66604 | 11/2000 |
| WO | WO 00/69560 | 11/2000 |
| WO | WO 00/78455 | 12/2000 |
| WO | WO 00/79285 | 12/2000 |

(Continued)

OTHER PUBLICATIONS

Bangs Laboratories, Inc., "Microsphere Detection Guide," http://www.bangslabs.com/products/bangs/guide.php, Aug. 2002.

(Continued)

Primary Examiner—Kenneth R. Horlick (57) ABSTRACT

Devices, methods, and kits for amplifying the signal from hybridization reactions between nucleic acid probes and their cognate targets are presented. The devices provide partially-duplexed, immobilized probe complexes, spatially separate from and separately addressable from immobilized docking strands. Cognate target acts catalytically to transfer probe from the site of probe complex immobilization to the site of immobilized docking strand, generating a detectable signal. The methods and kits of the present invention may be used to identify the presence of cognate target in a fluid sample.

34 Claims, 5 Drawing Sheets

FOREIGN PATENT DOCUMENTS

| | | |
|---|---|---|
| WO | WO 01/46465 | 6/2001 |
| WO | WO 01/47638 | 7/2001 |
| WO | WO 02/29112 | 4/2002 |

OTHER PUBLICATIONS

Bonnet et al., "Thermodynamic Basis of the Enhanced Specificity of Structured DNA Probes," *Proc. Natl. Acad. Sci. USA* 96: 6171-6176 (1999).

Braasch et al., "Locked Nucleic Acid (LNA): Fine-Tuning the Recognition on DNA and RNA," *Chem. Biol.* 8(1): 1-7 (2001).

Brenner et al., "In Vitro Cloning of Complex Mixtures of DNA on Microbeads: Physical Separation of Differentially Expressed cDNAs," *Proc. Natl. Acad. Sci. USA* vol. 97 No. 4: pp. 1665-1670 (2000).

Cambien et al., "Sequence Diversity in 36 Candidate Genes for Cardiovascular Disorders," *Am. J. Hum. Genet.* 65: 183-191 (1999).

Cargill et al., "Characterization of Single-Nucleotide Polymorphisms in Coding Regions of Human Genes," *Nature Genet.* 22: 231-238 (1999) (Erratum in: *Nat Genet* 23(3): 373 (Nov. 1999)).

Cargill et al., "Characterization of Single-Nucleotide Polymorphisms in Coding Regions of Human Genes," Erratum in: *Nat Genet* 23(3): 373 (Nov. 1999).

Conner et al., "Detection of Sickle Cell βs-globin Allele by Hybridization with Synthetic Oligonucleotides," *Proc. Natl. Acad. Sci. USA* 80(1): 278-282 (1983).

Corey et al., "Strand Invasion by Oligonucleotide-Nuclease Conjugates," *Bioconjugate Chem.* 6: 93-100 (1995).

Dubertet et al., "Single-Mismatch Detection Using Gold-Quenched Fluorescent Oligonucleotides," *Nature Biotechnology* 19: 365-370 (2001).

Guo et al., "Enhanced Discrimination of Single Nucleotide Polymorphisms by Artificial Mismatch Hybridization," *Nature Biotechnology* 15: 331-335 (1997).

Halushka et al., "Patterns of Single-Nucleotide Polymorphisms in Candidate Genes for Blood-Pressure Homeostasis," *Nature Genet.* 22: 239-247 (1999).

International SNP Map Working Group, "A Map of Human Genome Sequence Variation Containing 1.42 Million Single Nucleotide Polymorphisms," *Nature* 409: 928-933 (2001).

International Human Genome Sequencing Consortium, "Initial Sequencing and Analysis of the Human Genome," *Nature* 409: 860-921 (2001).

Johnson et al., "Strategies in Complex Disease Mapping," *Cur.. Opin. Genet. Dev.* 10(3): 330-334 (2000).

Kokoris et al., "High-Throughput SNP Genotyping with the Masscode System," *Mol Diagn.* 5(4): 329-340 (2000).

Kricka et al., "Comparison of 5-Hydroxy-2, 3-Dihydrophthalazine-1, 4-Dione and Luminol as Co-Substrates for Detection of Horseradish Peroxidase in Enhanced Chemiluminescent Reactions," *Journal of Immunoassay* vol. 17: pp. 67-83 (1996).

Kurakin et al., "Cooperative Strand Displacement by Peptide Nucleic Acid (PNA)," *Chemistry & Biology* 5(2): 81-89 (1998).

Lander et al., "The Chipping Forecast," *Supplement to Nature Genetics* vol. 21 No. 1: pp. 1-60 (Jan. 1999).

Leone et al., "Molecular Beacon Probes Combined with Amplification by NASBA Enable Homogeneous, Real-Time Detection of RNA," *Nucleic Acids Research* 26(9): 2150-2155 (1998).

Li et al., "A New Class of Homogeneous Nucleic Acid Probes Based on Specific Displacement Hybridization," *Nucleic Acids Research* 30(2): 1-9 (2002).

Li et al., "Low Nucleotide Diversity in Man," *Genetics* 129: 513-523 (1991).

Lundqvist et al., "Influence of Different Luminols on the Characteristics of the Chemiluminescence Reaction in Human Neutrophils," *J. Biolumin. Chemilumin.* vol. 10: pp. 353-359 (1995).

Lyer et al., "Modified Oligonucleotides—Synthesis, Properties, and Applications," *Curr. Opin. Mol. Ther.* 1(3): 344-358 (1999).

Nielsen, Peter E., "Peptide Nucleic Acid: A Versatile Tool in Genetic Diagnostics and Molecular Biology," *Curr. Opin. Biotechnol.* 12(1): 16-20 (2001).

Riley et al., "The Use of Single Nucleotide Polymorphisms in the Isolation of Common Disease Genes", *Pharmacogenomics* 1(1):39-47 (2000).

Thorpe et al., "Bioluminsense and Chemiluminescence; Chapter 29: Enhanced Chemiluminescent Reactions Catalyzed by Horseradish Peroxidase," *Methods in Enzymology* vol. 133: pp. 331-353 (1986).

Venter et al., "The Sequence of the Human Genome," *Science* 291: 1304-1351 (2001).

Verma et al., "Modified Oligonucleotides: Synthesis and Strategy for Users," *Annu. Rev. Biochem.* 67: 99-134 (1998).

Wittung et al., "Direct Observation of Strand Invasion by Peptide Nucleic Acid (PNA) into Double-Stranded DNA," *J. Am. Chem. Soc.* 118: 7049-7054 (1996).

\* cited by examiner

NONENZYMATIC CATALYTIC SIGNAL AMPLIFICATION FOR NUCLEIC ACID HYBRIDIZATION ASSAYS

STATEMENT OF GOVERNMENT SUPPORT

This invention was made in the course of U.S. contract no. NAS2-99092 awarded by NASA. The U.S. government has certain rights in this invention.

FIELD OF THE INVENTION

The present invention is in the field of molecular biology, and relates particularly to devices, methods, and kits for amplifying signals from hybridization reactions between nucleic acid probes and their cognate targets.

BACKGROUND OF THE INVENTION

Efforts to increase the sensitivity of nucleic acid hybridization reactions have been a recurrent feature of the molecular biology landscape for the past 30 years. Among other advantages, increases in sensitivity serve to decrease the amount of sample, probe, and other reagents required to detect a nucleic acid target, of particular importance when a biological sample occurs in limiting amount.

Early efforts were directed to increasing detection sensitivity in hybridization reactions performed using radiolabeled probes and included, for example, the development of methods for increasing the specific activity of radiolabeled probes, such as random primed hexamer labeling, and of methods that increased detection sensitivity itself, such as the use of rare earth intensifying screens at subzero film exposure temperatures. The later introduction of phosphorimaging techniques made possible the electronic amplification of radioactive signals.

Other efforts, not limited to radioisotopic labeling, have included alterations in probe composition, such as use of single-stranded RNA transcripts, and more recently, the introduction of peptide nucleic acids, respectively reducing competition and increasing the stability of the resulting probe:target duplex.

Enzymatic amplification of signal has also been used to increase sensitivity, with the enzyme variously catalyzing deposition of optically detectable colored product or, in the case of enhanced chemiluminescence, catalyzing the production of light.

More recently, improvements in sensitivity have been attained by physical amplification of target, either before or during detection. The advantages of target amplification—including the ability to start with picomolar amounts of starting material, the ability to decrease the complexity of a sample by specific amplification of a desired sequence, and the ability to monitor amplification in real time—have led to a variety of amplification protocols, such as polymerase chain reaction (PCR), nucleic acid sequence-based amplification (NASBA), self-sustained sequence recognition (3SR), ligase chain reaction (LCR), transcription-mediated amplification (TMA), rolling circle amplification (RCA), and strand displacement amplification (SDA).

Yet all of these approaches have disadvantages.

For example, there is a physical limit to the number of labels that can be incorporated into a probe of given length. Enzymatic methods for amplifying signal require careful attention to technique, and may require expensive reagents. Physical amplification of target suffers from nonspecific amplification; where mispriming occurs early in the amplification reaction, the erroneous template may be amplified to nearly as great an extent as the desired target. Additionally, methods of target amplification that require thermocycling require additional apparatus, and may preclude real-time detection when the sensitivity of the detection means is itself affected by changes in temperature.

Hammond et al., U.S. Pat. No. 6,255,051, taking a different approach, recently described a "recursive cascade" of strand displacement reactions with gain of signal at each individual displacement reaction, which is said to lead to signal amplification. However, the scheme requires at least seven engineered probe molecules for each target to be detected.

There thus exists a continuing need in the art for methods, devices, compositions and kits for amplifying the signal in nucleic acid hybridization reactions, and particularly for nonenzymatic, isothermal methods for amplifying the signal without physical amplification of target.

SUMMARY OF THE INVENTION

The present invention solves these and other needs in the art by providing a simplified, two-step, strand displacement reaction protocol in which a target nucleic acid acts catalytically to amplify the signal resulting from its specific hybridization to a nucleic acid probe. The reaction is nonenzymatic and isothermal, and is readily adapted to a variety of labels and detection means.

In a first aspect, the invention provides a device for nonenzymatically amplifying the signal from a hybridization reaction between at least a first nucleic acid probe and its cognate nucleic acid target present in fluid solvent.

The device comprises at least one substrate; a first plurality of probe complexes, each having a probe nucleic acid strand and a displacement nucleic acid strand hybridized thereto, the plurality of probe strands being identical to one another and the plurality of displacement strands being identical to one another; and a first plurality of identical docking nucleic acid strands.

The displacement strands and the docking strands are immobilized to one of the at least one substrates, the immobilized displacement strands and immobilized docking strands being spatially segregated from one another, separately addressable, and fluidly communicating upon contact of the device with fluid solvent.

The probe strand of the probe complexes has at least three regions: a first region that is substantially complementary to a region of each of the displacement strand, the target, and the docking strand; a second region that is substantially complementary to a region of each of the target and the docking strand, but not substantially complementary to a region of the displacement strand; and a third region that is substantially complementary to a region of the docking strand, but not substantially complementary to a region of either of the displacement strand or the target.

Contact of target to the device catalyzes transfer, by two successive strand displacement reactions, of the probe strands from their original address at the site of immobilization of the displacement strands, to a final address at the spatially segregated, separately addressable, site of attachment of the docking strands. The transfer of the probe generates a detectable signal.

The substrate may be a unitary substrate, such as a substrate having a planar surface to which the displacement strands and docking strands are segregably attached. Alternatively, the unitary substrate may be at least one internal wall of a capillary, channel, or chamber formed in the device. The unitary substrate may, in illustrative embodiments, comprise glass, silicon, or plastic.

The substrate may instead be nonunitary, such as a collection of beads, or electrodes of an electrode array, including a nanowire electrode array.

The probe strands may optionally further comprise one or more signaling moieties, such as an optically detectable moiety, such as a fluorophore, an electrochemically detectable signaling moiety, such as a polyguanidine polymer or ferrocenyl group, a radioactive moiety, or a moiety that is mass spectrally detectable.

The displacement strand, probe strand, and displacement strand may be designed to tune the probe's ability selectively to discriminate among polymorphic variants of the target. The device may be designed to discriminate targets that differ from one another by three or more nucleotides, two or more nucleotides, or even a single nucleotide (single nucleotide polymorphism).

In these and other illustrative embodiments, the second and third regions of the probe strands may independently be 2–14 nucleotides in length, 2–10 nucleotides in length, or even 2–6 nucleotides in length.

In various embodiments, any or all of the probe strands, displacement strands, and docking strands may be peptide nucleic acids or include locked nucleic acid analogues.

The devices of the present invention may be used to detect a single target, or a plurality of targets in a multiplexed reaction.

To detect a plurality of targets, the device of the present invention further comprises at least a second plurality of probe complexes and at least a second plurality of docking strands. The displacement strands, probe strands, and docking strands of the at least second pluralities are respectively identical thereamong but differ from those of the first plurality, and the first and second regions of the additional pluralities are substantially complementary to at least a second cognate nucleic acid target.

In certain embodiments, the additional pluralities of probe strands are distinguishably labeled from the first plurality of probe strands, as by labeling with fluorophores having optically distinguishable excitation or emission spectra.

In a second aspect, the invention provides a method of detecting a hybridization reaction between a nucleic acid probe and its cognate nucleic acid target with a catalytically amplified signal.

The method comprises contacting the target, in a fluid solvent—for example, within an aqueous composition—to a device according to the present invention. In the device, the first and second regions of the probe strands are substantially complementary to the target and the target thus catalyzes transfer of the probe strand from its original address at the site of displacement strand immobilization to the spatially segregated, separately addressable, site of docking strand immobilization. The transfer of the probe generates a signal, which is then detected.

The signal may be either or both of a diminution in probe concentration at its original address or an increase in probe concentration at the final address. In embodiments in which the probe strand is labeled, the signal may be either or both of a diminution in detectable signal at the original probe address or an increase in signal at the final probe address.

The signal may be optically detectable, such as fluorescence emission, electrochemically detectable, or mass spectrally detectable.

The detection methods of the present invention may include an additional step, after contacting the device with sample and before detecting signal, of separating the immobilized docking strands from the fluid solvent.

In a third aspect, the invention provides a kit for nonenzymatically amplifying the signal from a hybridization reaction between at least a first nucleic acid probe and its cognate nucleic acid target present in fluid solvent.

The kit comprises a device of the present invention having immobilized displacement strands and immobilized docking strands, but in which the probe strands have not been heteroduplexed to the displacement strands, and a composition comprising such probe strands. Thus, the kit permits the device to be readied for use immediately before sample addition, obviating any instability of probe duplexes that might preclude long term storage of the amplification device.

Accordingly, the kit comprises a device that comprises at least one substrate, a first plurality of identical displacement nucleic acid strands, and a first plurality of identical docking nucleic acid strands. The displacement strands and the docking strands are immobilized to one of the at least one substrates, the immobilized displacement strands and immobilized docking strands being spatially segregated from one another, separately addressable, and fluidly communicating upon contact of the device with fluid solvent. The kit further comprises a composition that comprises probe nucleic acid strands, the probe nucleic strands having at least three regions: a first region that is substantially complementary to a region of each of the displacement strand, the target, and the docking strand; a second region that is substantially complementary to a region of each of the target and the docking strand, but not substantially complementary to a region of the displacement strand; and a third region that is substantially complementary to a region of the docking strand, but not substantially complementary to a region of either of the displacement strand or the target.

In some embodiments of the kits of the present invention, the probe strands are detectably labeled. In other embodiments, the kit further comprising reagents for detectably labeling the probe strands of the included composition. In yet other embodiments, the kit further comprises a control composition, the control composition including target nucleic acids, typically at defined concentration, that are capable of catalyzing transfer of the probes from the displacement strands of the device to the docking strands of the device.

Further features of the invention, its nature and various advantages will be more apparent from the accompanying drawings and the following detailed description.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION

The present invention provides devices, methods, and kits for nonenzymatic, isothermal, catalytic amplification of the signal from a hybridization reaction between a nucleic acid probe and its cognate target. The amplified signal facilitates detection of a nucleic acid target.

Figure 1:
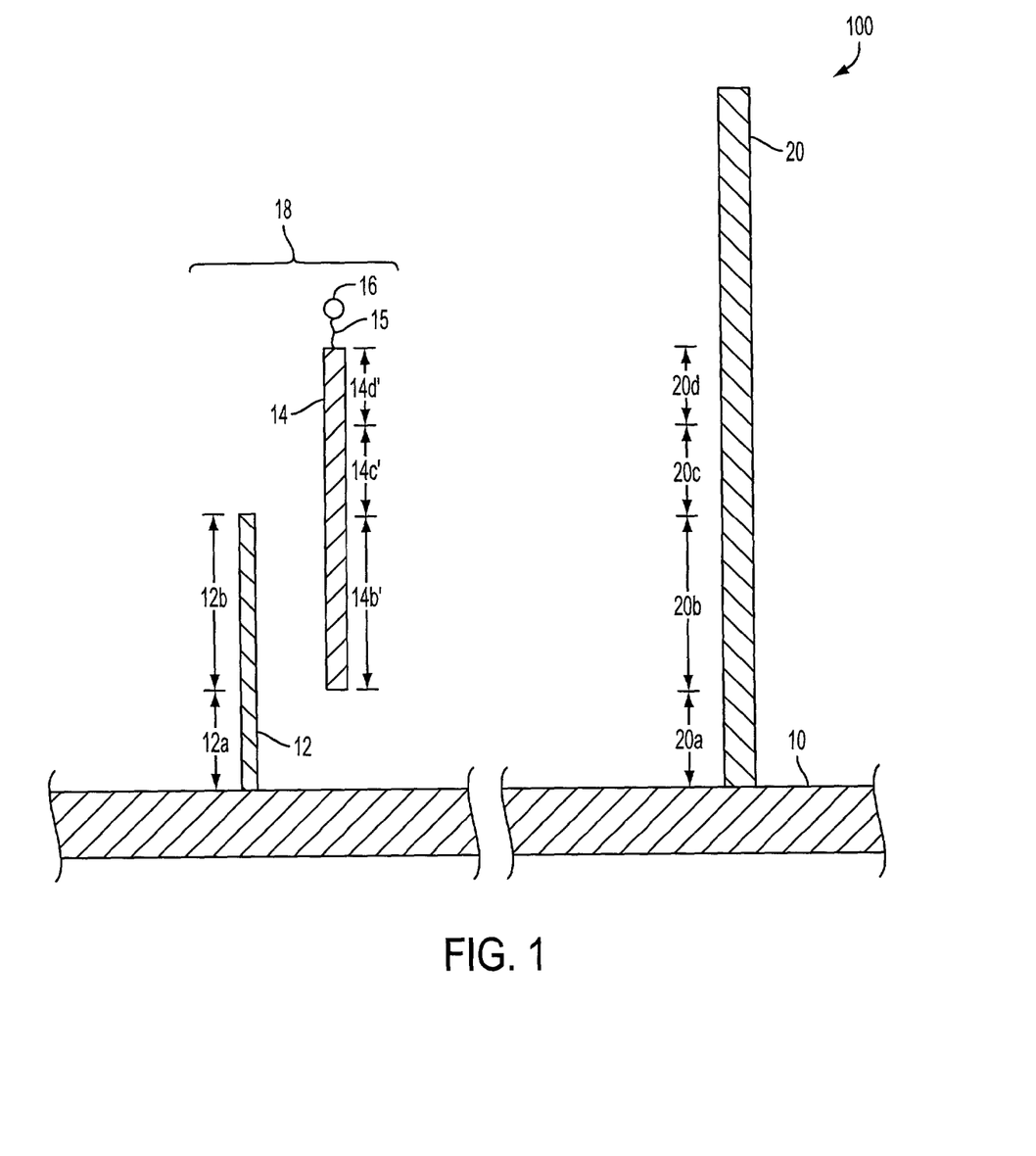
FIG. 1 shows an illustrative device for catalytically amplifying the signal from a hybridization reaction, according to the present invention.

FIG. 1 schematizes an illustrative device for performing an illustrative method of the present invention.

Device 100 comprises substrate 10. As more fully described below, substrate 10 is any substrate to which a single-stranded nucleic acid may be attached, either covalently or noncovalently. In the illustrative embodiment shown in FIG. 1, substrate 10 includes a planar surface to which nucleic acids are attached.

Single-stranded nucleic acid 12, herein also called a "displacement strand", and single-stranded nucleic acid 20, herein also called a "docking strand", are attached to substrate 10. Displacement strand 12 and docking strand 20 may be attached to substrate 10 at their respective 3' termini, 5' termini, or via internal nucleotides.

Docking strand 20 is attached to substrate 10 at any site that is spatially distinct and separately addressable from the site of attachment of displacement strand 12, and that can be placed in fluid communication therewith. Although the sites of attachment of displacement strand 12 and docking strand 20 are shown in FIG. 1 as spatially segregated sites on a unitary substrate 10, displacement strand 12 and docking strand 20 may be attached to separate and discrete (i.e., nonunitary) substrates 10, so long as the sites of attachment are separately addressable and can be placed in fluid communication with one another.

For illustrative purposes, FIG. 1 shows a single displacement strand 12 and a single docking strand 20. In typical embodiments, however, a plurality of displacement strands 12, either identical to one another or different from one another, are attached to substrate 10. Similarly, a plurality of docking strands 20, either identical or nonidentical to one another, are typically attached to substrate 10.

Single-stranded nucleic acid strand 14, herein also denominated the "probe strand", is hybridized to displacement strand 12 by Watson-Crick basepairing to form strand displacement probe complex 18.

Probe strand 14 comprises at least three regions: a first region (region 14b') that is substantially complementary to a region of each of displacement strand 12, cognate target strand 22 (see FIGS. 2A and 2B), and docking strand 20; a second region (region 14c') that is substantially complementary to a region of each of cognate target 22 and docking strand 20, but that is not substantially complementary to a region of displacement strand 12; and a third region (region 14d') that is substantially complementary to a region of docking strand 20, but not substantially complementary to a region of either of displacement strand 12 or cognate target strand 22.

By "substantially complementary" is intended a degree of sequence complementarity sufficient to provide a stable duplex under desired hybridization conditions, typically high stringency or medium stringency aqueous or formamide-containing conditions. By "cognate target" is intended a nucleic acid intended specifically to be detected by probe 14; that is, a nucleic acid as to which probe 14 is sufficiently complementary as to permit its specific detection.

Probe 14 is hybridized to displacement strand 12 in complex 18 by hybridization of probe region 14b' to displacement region 14b, which is substantially complementary thereto.

Probe strand regions 14c' and 14d', which are not substantially complementary to a region of displacement strand 12, remain single-stranded in probe complex 18.

Docking strand 20 has at least three regions, 20b, 20c, and 20d: region 20b is substantially complementary to probe strand region 14b'; region 20c is substantially complementary to probe strand region 14c'; region 20d is substantially complementary to probe strand region 14d'.

Figure 2A:
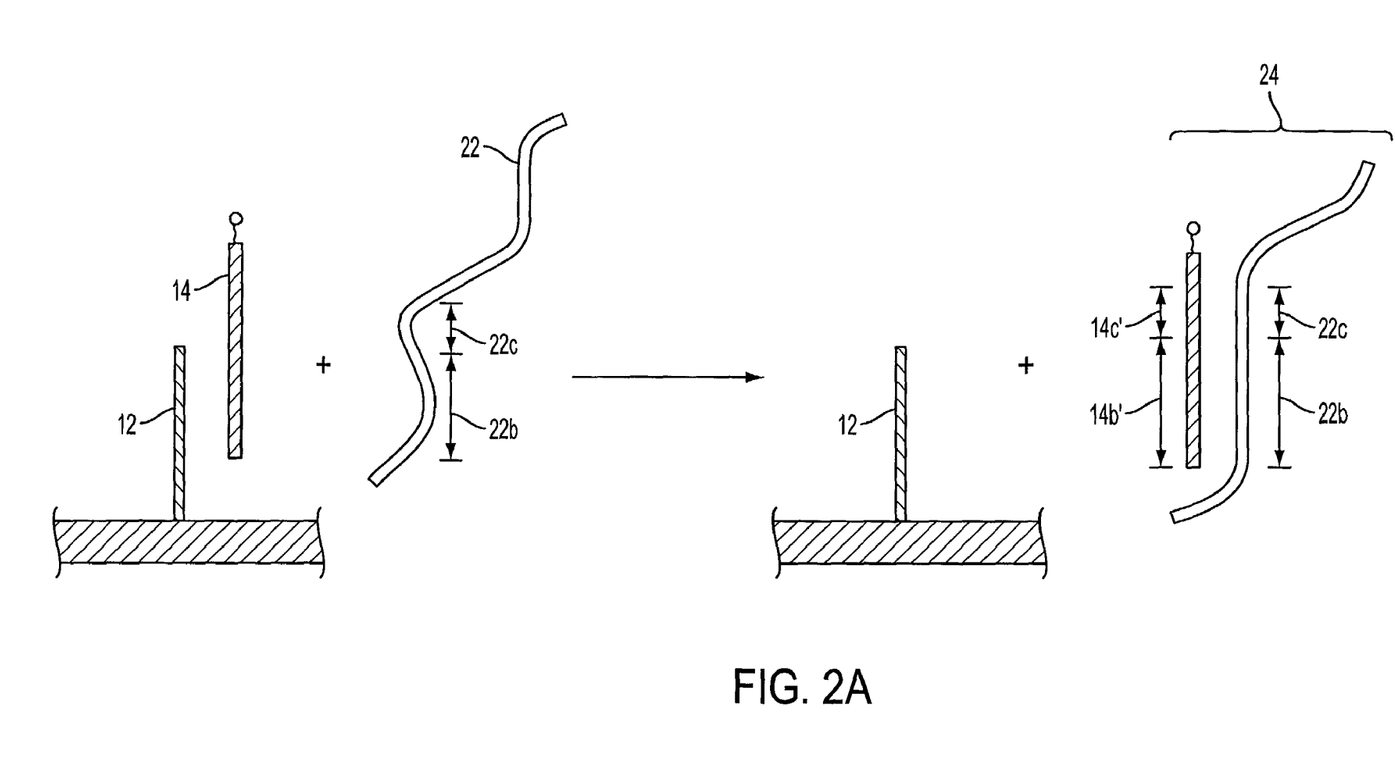
FIG. 2A shows a first spontaneous reaction step following contact of the device of FIG. 1 with a target nucleic acid in an illustrative method of the present invention.
Figure 2B:
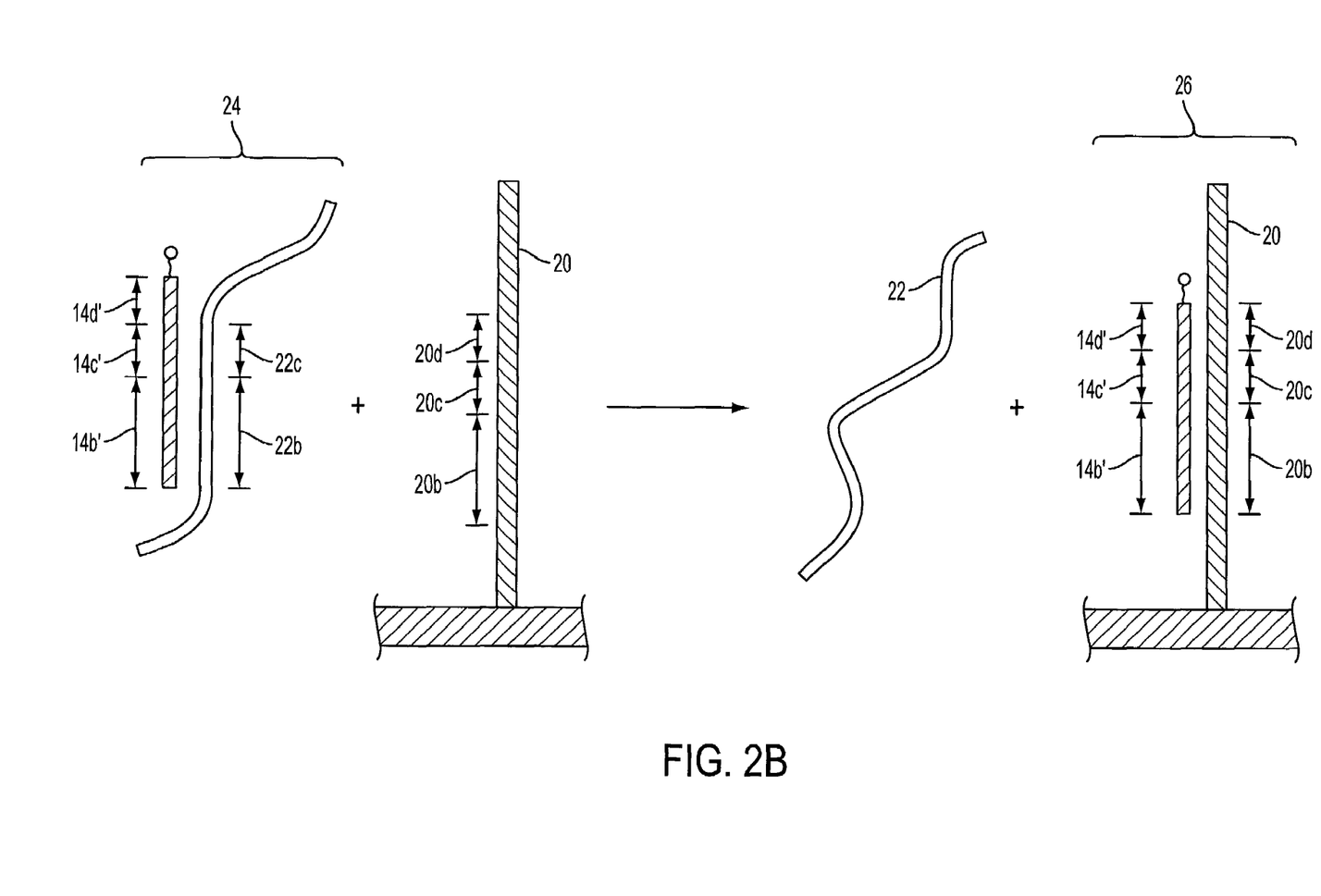
FIG. 2B shows a second spontaneous reaction step following contact of the device of FIG. 1 with a target nucleic acid in an illustrative method of the present invention.

FIGS. 2A–2C schematize an illustrative method of the present invention performed using the illustrative device of FIG. 1.

As shown in FIG. 2A, substrate-attached probe complex 18 is contacted with single-stranded target nucleic acid strand 22 in a fluid solvent, typically as an aqueous composition.

Upon contact, target strand 22 displaces probe strand 14 from probe complex 18. The displacement reaction creates a fluidly mobile target complex 24, comprising target strand 22 hybridized to probe strand 14, leaving displacement strand 12 attached, in single-stranded form, to substrate 10 at its original address.

Target strand 22 includes at least two regions: target region 22b, which is substantially complementary to probe strand region 14b', and target region 22c, which is substantially complementary to probe strand region 14c'.

Displacement of probe strand 14 from displacement strand 12 is initiated by the interaction of target region 22c with single-stranded probe region 14c', which is substantially complementary thereto. Completion of the displacement reaction is driven by the increased stability (lower enthalpy) of target complex 24 as compared to probe complex 18, which is in turn due to the increase in length of the duplexed region of the probe in target complex 24: as schematized in FIG. 3B, the duplexed region in fluidly mobile target complex 24 spans probe regions 14b'–14c'; by contrast, the duplexed region in original probe complex 18 traverses only probe region 14b'.

FIG. 2B shows a second reaction step. Fluidly mobile target complex 24 contacts docking strand 20. As more fully discussed below, target complex 24 may contact docking strand 20 by simple diffusion through the fluid phase of the hybridization reaction, or may contact docking strand 20 by movement that is further motivated by bulk fluid flow, electrical field, or other external forces.

Docking strand 20 then displaces target strand 22 from target complex 24.

Docking strand region 20d initiates displacement through interaction with probe single-stranded region 14d'. Completion of the displacement reaction is driven by the increased stability (lower enthalpy) of the resulting docking complex 26 as compared to target complex 24, which is attributable to the longer span of duplex in the final docking complex: as schematized in FIG. 3B, the duplexed region of docking complex 26 spans probe regions 14b'–14c'–14d'; by contrast, the duplexed region of fluidly mobile target complex 24 spans only probe regions 14b'–14c'.

The displacement reaction immobilizes probe 14 at the docking strand address, that is, at the site of attachment of docking strand 20 to substrate 10, and liberates target 22, which is then free to contact a new probe complex 18 in a new iteration of the reaction set forth in FIGS. 2A and 2B.

Figure 3A:
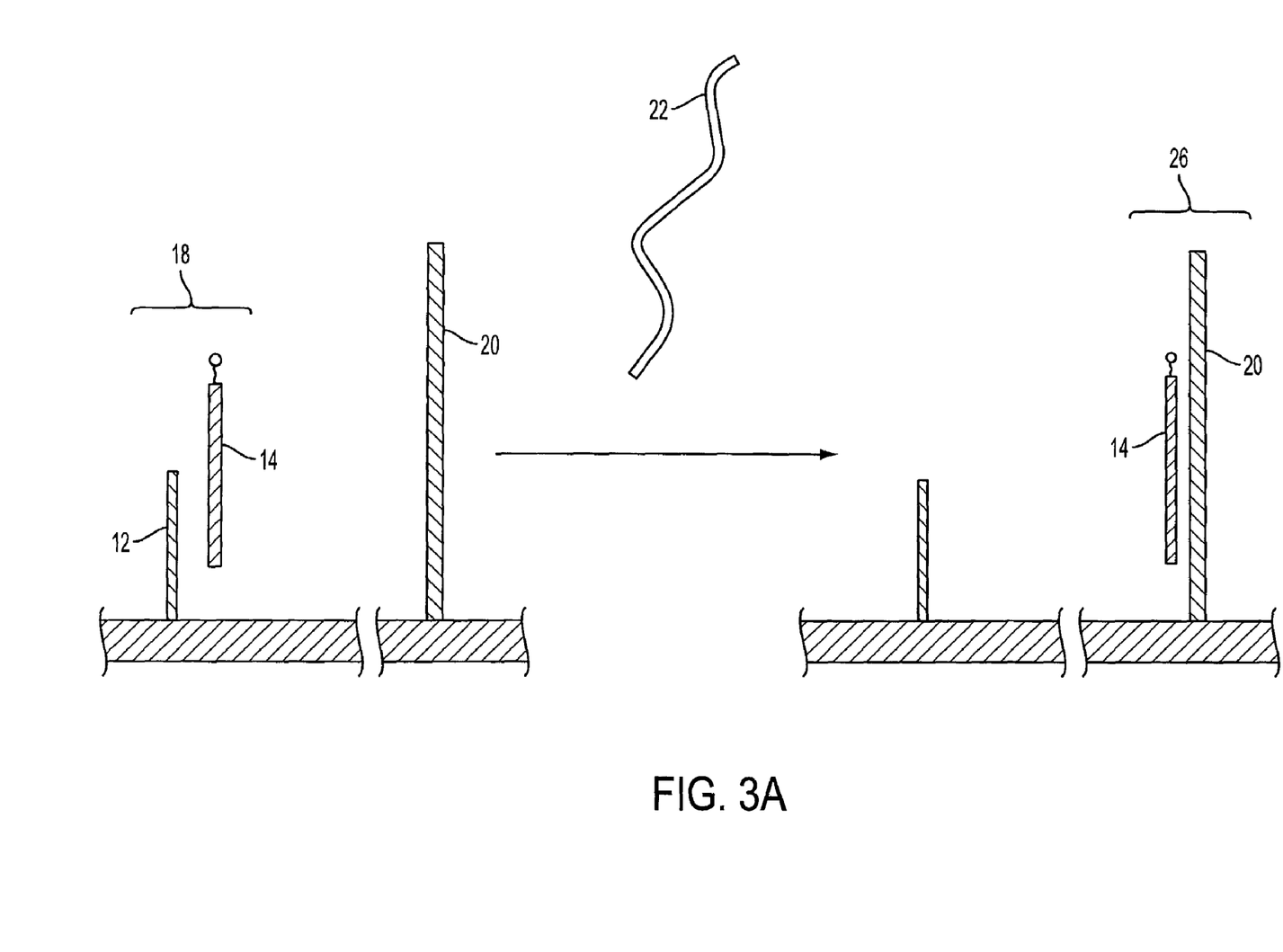
FIG. 3A summarizes the overall reaction, individual steps of which are shown in FIGS. 2A and 2B, particularly demonstrating the catalytic action of the target nucleic acid in effecting probe transfer in an illustrative method of the present invention.
Figure 3B:
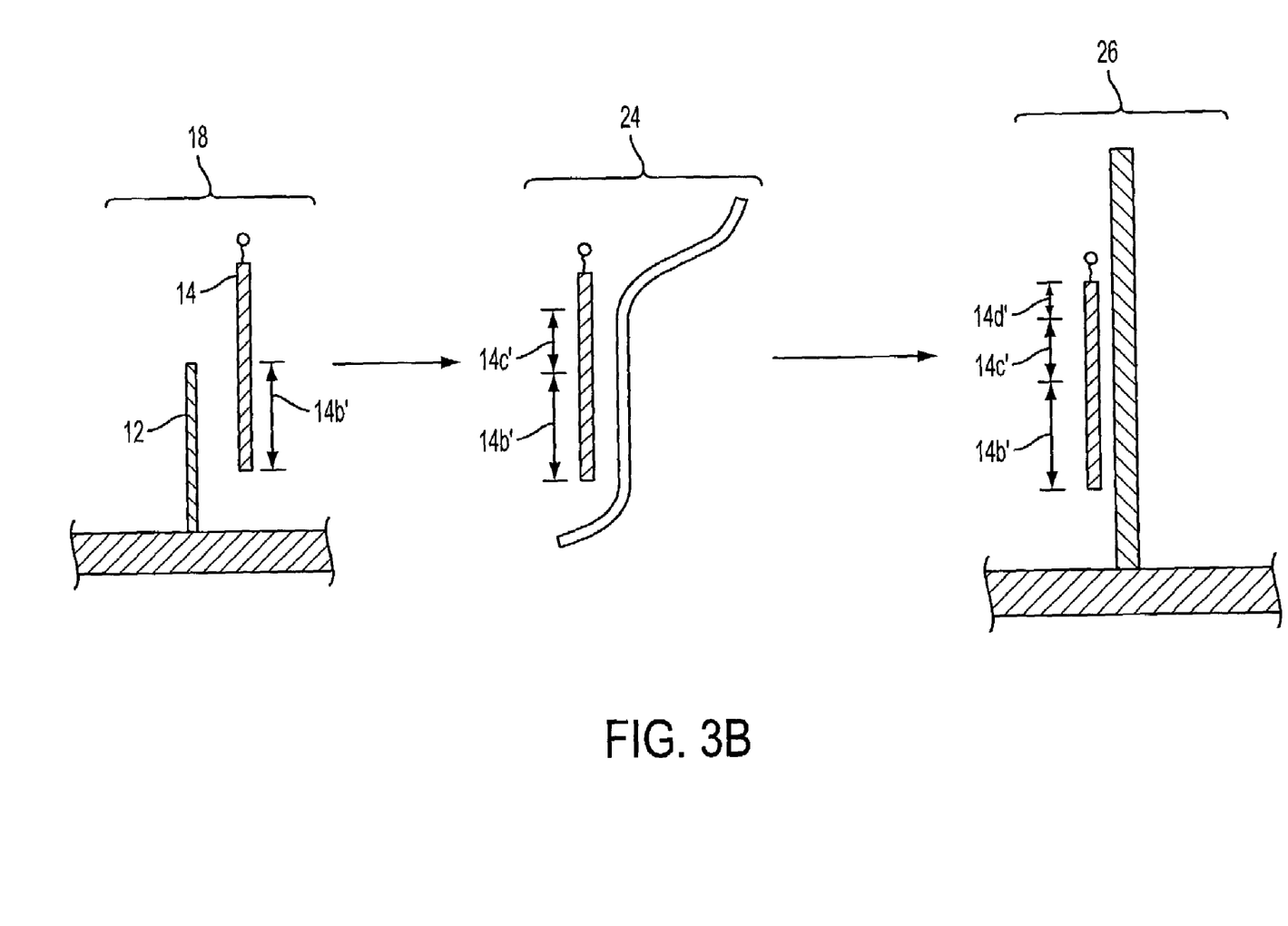
FIG. 3B illustrates the successively increased length of the duplexed region of the nucleic acid probe through the reaction steps in an illustrative method of the present invention.

FIG. 3A summarizes the overall reaction, making explicit that target strand 22 acts catalytically to effect transfer of probe strand 14 from its original address at the site of substrate attachment of displacement strand 12 to the substrate attachment site of docking strand 20. The limiting substrates for the catalytic reaction are probe complexes 18 and corresponding docking strands 20, and the reaction can continue until either one or both is exhausted.

The transfer of the probe from its original to final address may generate a detectable signal at either or both of the displacement strand address or docking strand address. For example, probe strand 14 may be labeled, such as by attachment of optional signaling moiety 16, which may be coupled to probe strand 14 through optional linker 15. Accordingly, the presence of target may be detected by either or both of diminution of signal at the original probe address or increase of signal at the final probe address.

Returning to FIG. 1, substrate 10 of device 100 may be any substrate to which a single-stranded nucleic acid may be attached, either covalently or noncovalently, in or upon which the sites of attachment may be separately addressed and placed in fluid communication with one another.

Substrate 10 may be porous. For example, substrate 10 may be a bibulous or nonbibulous membrane filter. Filters for nucleic acid attachment and detection are well known in the molecular biology, and include, for example, filters comprising nitrocellulose, nylon, or positively-charged derivatized nylon.

Substrate 10 may, conversely, be nonporous, and may conveniently be a material commonly used for construction of nucleic acid microarrays, such as a glass slide, surface-derivatized glass slide, or silicon wafer, or may usefully comprise any of a variety of laboratory-grade plastics. Plastic substrates may usefully be selected from the group consisting of polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, and mixtures thereof.

Substrate 10 may, but need not, be planar or include a planar surface.

For example, device 100 of the present invention may conveniently be shaped as a cuvette, one or more internal surfaces of which serve as substrate 10. Alternatively, device 100 of the present invention may include channels, chambers, or tubes—for example as parts of a microfluidic device—with one or more internal surfaces of such channels, chambers, or tubes serving as substrate 10. Device 100 may be shaped as a disc, such as an optical disc, with substrate 10 being one or more surfaces upon or within the disc, the spinning of the disc usefully serving to motivate fluid movement by centripetal force.

Substrate 10 may be unitary, providing sites of attachment on a single substrate for both displacement strand 12 and docking strand 20.

Substrate 10 may instead be nonunitary, distributing displacement strand 12 and docking strand 20 onto different substrates that are separately addressable and that, upon common contact with a fluid solvent, are placed in fluid communication with one another.

Substrate 10 may, for example, be a surface of a bead, or pellet, such as a glass bead, with displacement strand 12 and docking strand 20 distributed onto different beads. The beads, in these embodiments, are separately addressable, and can be placed in fluid communication with one another upon mutual contact with a fluid solvent.

The beads need not be spherical. In addition, the beads may be porous, thus increasing the surface area of the bead available for assay. Bead sizes usefully range from nanometers, e.g. 100 nm, to millimeters, e.g. 5 mm, usefully from about 0.2 micron to about 200 microns, with beads from about 0.5 to about 5 microns being typical.

Suitable bead compositions include those used in peptide, nucleic acid and organic moiety synthesis, and include, for example, plastics, such as polystyrene, methylstyrene, acrylic polymers, ceramics, glass, paramagnetic materials, titanium dioxide, latex, cross-linked dextrans, cellulose, and nylon. See, e.g., "Microsphere Detection Guide" (Bangs Laboratories, Inc., http://www.bangslabs.com/products/bangs/guide.php).

In another illustrative example of nonunitary substrates 10 in the devices of the present invention, device 100 may comprise an array of electrodes, with each separately addressable electrode presenting on its surface a substrate 10 onto which displacement strands 12 and docking strands 20 may distributably be attached.

Arrays of nanowire electrodes, such as arrays of carbon nanotubes with covalently attached nucleic acids, and methods for their manufacture, are described in commonly owned and copending application Ser. Nos. 10/117,965, which is abandoned, and 10/117,866, which issued as U.S. Pat. No. 6,831,017 on Dec. 14, 2004, both filed Apr. 5, 2002, and commonly owned provisional application Ser. No. 60/370,763, filed Apr. 5, 2002, the disclosures of which are incorporated herein by this reference in their entireties.

Displacement strand 12 and docking strand 20 are attached to substrate 10 by covalent, noncovalent, or strong coordinate bond interactions.

Covalent attachment may be effected, for example, by spotting an amine derivatized nucleic acid onto a silylated glass surface, followed by covalent bonding upon sodium borohydride reduction. In another illustrative approach, covalent attachment may be effected by contacting an amine derivatized nucleic acid to a substrate bearing surface epoxy groups.

Noncovalent attachment may be direct or indirect. Direct noncovalent bonding may readily be effected, e.g., by spotting the nucleic acid onto a glass or derivatized glass surface in admixture with a chaotrope. Indirect noncovalent attachment may readily be accomplished by derivatizing the nucleic acid with one member of a specific binding pair, such as biotin, the other member of the binding pair, such as streptavidin, being attached to substrate 10.

Nucleic acids may be attached by coordinate, or dative, bonding between, e.g., a thiolated nucleic acid and a gold or platinum substrate 10.

Other methods of attaching nucleic acids to support surfaces are well known in the art.

Displacement strand 12, immobilized to substrate 10, hybridizes to probe strand 14, which is not attached to substrate 10, to create a partially duplexed strand displacement probe complex 18. The duplexed region is formed between displacement strand region 12b and substantially complementary probe region 14b'.

Displacement strand 12 may further comprise additional regions, such as region 12a as shown in FIG. 1, that are not substantially complementary to regions of probe 14. The one or more additional regions of displacement strand 12 may be disposed more proximally to substrate 10 than is region 12b, as illustrated, or may be disposed more distally to substrate 10 than is region 12b.

Region 12b of displacement strand 12 may be as short as 15 nucleotides in length, 20 nucleotides in length, or even as short as 25 nucleotides in length. Region 12b may be greater than 25 nucleotides in length, including at least 50 nucleotides in length, 75 nucleotides in length, even 100 nucleotides in length or more, such as 250 nucleotides, 500 nucleotides, even 1000 nucleotides or more in length, although lengths of 25 –250 nt are more typical.

Displacement strand 12 as a whole may be as short as 15 nucleotides in length, 20 nucleotides in length, or even as short as 25 nucleotides in length, particularly when displacement strand 12 lacks regions additional to region 12b. More typically, displacement strand 12 may be greater than 25 nucleotides in length, including at least 50 nucleotides in length, 75 nucleotides in length, even 100 nucleotides in length or more, such as 250 nucleotides, 500 nucleotides, even 1000 nucleotides or more in length, although lengths of 25 –250 nt are more typical.

Additional considerations that may be used in designing the size and sequence of displacement strand 12 are further described below.

Probe region 14b', which is substantially complementary to displacement strand region 12b, may be as short as 15 nucleotides in length, 20 nucleotides in length, or even as short as 25 nucleotides in length. Probe region 14b' may be greater than 25 nucleotides in length, including at least 50 nucleotides in length, 75 nucleotides in length, even 100 nucleotides in length or more, such as 250 nucleotides, 500 nucleotides, even 1000 nucleotides or more in length, although lengths of 25 –250 nt are more typical.

Probe regions 14c' and 14d' may each independently be as short as 2 nucleotides (nt), 3 nt, 4 nt, 5 nt, 6 nt, 7 nt, 8 nt, 9 nt, even 10 nt. Region 14c' may be greater than 10 nt, such as 11 nt, 12 nt, 13 nt, 14 nt, 15 nt, 16 nt, even 20 nt, 25 nt, 30 nt, 40 nt, 50 nt or even longer.

Probe regions 14b' and 14c', which are substantially complementary to target regions 22b and 22c, may be contiguous to one another in probe 14, as illustrated in FIGS. 2A and 2B. However, such geometry is not required. Probe region 14d', which is complementary only to region 20d of docking strand 20, may be contiguous to probe regions 14b' and 14c', as shown in FIGS. 2A and 2B, but such geometry is not required.

Probe 14 may further include nucleic acid regions additional to regions 14b', 14c', and 14d', which regions are not substantially complementary to any one or more of displacement strand 12, target strand 22, or docking strand 20. Such additional regions may be located at either end of probe 14, or may be interposed between or among any of probe regions 14b', 14c', and 14d'.

Probe strand 14 may also be labeled, as by inclusion of an optional signaling moiety 16 (also termed a "label"), optionally attached via a linker 15.

Probe strand 14 may, for example, have an optically detectable label, a mass spectrally detectable label, a label detectable by electrochemical means, or a radioactive label.

Optically detectable labels include moieties that fluoresce, moieties that luminesce, moieties that phosphoresce, and moieties that provide optically detectable calorimetric changes.

Fluorescent labels for nucleic acid detection are well known in the art, and include, for example, CyDyes™, such as Cy3, Cy3B, Cy3.5, Cy5, Cy5.5, Cy7 (Amersham Biosciences, Inc., Piscataway, N.J.), fluorescein isothiocyanate (FITC), Texas Red™ (Molecular Probes, Eugene, Oreg.), and Alexa Fluor dyes, such as Alexa Fluor 350, 430, 488, 532, 546, 568, 594, 633, 647, 660, 680, 700 and Alexa Fluor 750 dyes (all from Molecular Probes, Eugene, Oreg.).

Luminescent labels, such as enhanced chemiluminescence labels, are well known in the art. For example, in the presence of hydrogen peroxide ($H_2O_2$), horseradish peroxidase (HRP) can catalyze the oxidation of cyclic diacylhydrazides, such as luminol; the luminol excited state then decays to the ground state by emitting light. Strong enhancement of the light emission is produced by enhancers, such as phenolic compounds. Advantages include high sensitivity, high resolution, and rapid detection without radioactivity. See, e.g., Thorpe et al., *Methods Enzymol.* 133:331–53 (1986); Kricka et al., *J. Immunoassay* 17(1):67–83 (1996); and Lundqvist et al., *J. Biolumin. Chemilumin.* 10(6):353–359 (1995), the disclosures of which are incorporated herein by reference in their entireties. Kits for such chemiluminescent and enhanced chemiluminescent detection of nucleic acids are commercially available.

Colorimetrically detectable labels include enzymes that can lead to local precipitation of optically-detectable colored products; such enzymes may be conjugated directly to probe 14 or, more typically, through a second step interaction mediated by members of a specific binding pair, such as biotin, which is readily incorporated into nucleic acids, and streptavidin, which can readily be conjugated to enzymes.

Enzymes useful for calorimetric detection are well known, and include alkaline phosphatase, β-galactosidase, glucose oxidase, horseradish peroxidase (HRP), and urease. Typical substrates for production and deposition of visually detectable products include o-nitrophenyl-beta-D-galactopyranoside (ONPG); o-phenylenediamine dihydrochloride (OPD); p-nitrophenyl phosphate (PNPP); p-nitrophenyl-beta-D-galactopyranoside (PNPG); 3',3'-diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Labels that are detectable by mass spectrometry, "mass tags", may also be used. Mass tags can be designed to provide hundreds of mass spectrally distinguishable species, allowing highly multiplexed reactions, and can be designed to be cleavable, typically photochemically cleavable, from the labeled nucleic acid, simplifying analysis. For nucleic acid hybridization assays, mass tags can provide quantitative, femtomolar sensitivity. See, e.g., Kokoris et al., *Mol Diagn.* 5(4):329–40 (2000). The mass of the probe itself may alternatively be detected, with or without an additional signaling mass attached thereto, for example by surface plasmon resonance techniques.

Electrochemical signaling moieties include, for example, polyguanidine nucleic acid polymers and molecules comprising a ferrocenyl moiety.

Either or both of displacement strand 12 and docking strand 20 may also optionally be labeled.

For example, when probe 14 is labeled with a fluorophore, either or both of displacement strand 12 and docking strand 20 may be labeled with one or more fluorophores capable of fluorescence energy resonance transfer (FRET) with the fluorophore of probe 14.

Pairs of fluorophores useful for FRET are well known in the art, and include, e.g., fluorescein isothiocyanate (FITC) and tetramethylrhodamine isothiocyanate (TRITC); FITC/Texas Red™ (Molecular Probes, Inc.); FITC/N-hydroxysuccinimidyl 1-pyrenebutyrate (PYB); FITC/eosin isothiocyanate (EITC); FITC/tetramethylrhodamine (TAMRA); and various Alexa Fluor pairs (Molecular Probes, Inc.), such as Alexa Fluor 488 and any one of Alex Fluors 546, 555, 568, 594, or 647.

When probe 14 is labeled with a fluorophore, either or both of displacement strand 12 and docking strand 20 may instead optionally be labeled with a fluorescence quencher. Conversely, probe 14 may be labeled with a fluorescence quencher and either or both of displacement strand 12 and docking strand 20 may be labeled with a fluorophore.

Suitable fluorophore-quencher pairs are well known in the art, and include, e.g., FAM, HEX, TAMRA, EDANS and Texas Red™ as fluorophore, with dabcyl useful as a common quencher. Other quenchers include, e.g., QSY 7, QSY 9, QSY 21 and QSY 35 (all from Molecular Probes, Inc., Eugene, Oreg.); gold nanoparticles (Dubertret et al., Nature Biotechnol. 19:365–370 (2001)), and other metals and metalloids, both as macroscopic solids and nanoparticles, including particles in colloid suspension.

Displacement strand 12, probe strand 14, and docking strand 20 comprise nucleic acids.

The nucleic acid may be a natural nucleic acid comprising natural nucleotides in natural 5'–3' phosphodiester linkage, such as DNA or RNA, or chimeras thereof, or may instead be a nonnatural nucleic acid analogue, comprising one or more of modified bases, modified sugars, or modified linkages. A wide variety of nucleic acid analogues, and chemistries for their synthesis, are now well known in the molecular biological art. See, e.g., Verma et al., " Modified oligonucleotides: synthesis and strategy for users," *Annu. Rev. Biochem.* 67:99–134 (1998) and Lyer et al., "Modified oligonucleotides—synthesis, properties and applications," *Curr. Opin. Mol. Ther.* 1(3):344–58 (1999), the disclosures of which are incorporated herein by reference in their entireties.

Among nucleic acid analogues that may be used for any or all of the displacement strand, probe strand, or docking strand in the devices, methods and kits of the present invention are peptide nucleic acids (PNA). In PNA compounds, the phosphodiester backbone of the nucleic acid is replaced with an amide-containing peptide backbone; nucleobases are bound directly or indirectly to aza nitrogen atoms of the amide portion of the backbone, typically by methylene carbonyl linkages. See, e.g., Nielsen, *Curr. Opin. Biotechnol.* 12(1):16–20 (2001), the disclosure of which is incorporated herein by reference in its entirety.

Also particularly useful are locked nucleic acid (LNA) analogues. LNAs are bicyclic and tricyclic nucleoside and nucleotide analogues and the oligonucleotides that contain such analogues. The basic structural and functional characteristics of LNAs and related analogues are disclosed in various publications and patents, including WO 99/14226, WO 00/56748, WO 00/66604, WO 98/39352, U.S. Pat. No. 6,043,060, and U.S. Pat. No. 6,268,490, all of which are incorporated herein by reference in their entirety. See also, Braasch et al., "Locked nucleic acid (LNA): fine-tuning the recognition of DNA and RNA," *Chem. Biol.* 8(1):1–7 (2001), incorporated herein in its entirety by reference.

Although a single displacement strand 12 and single docking strand 20 may be attached to substrate 10 of device 100, signal amplification requires catalytic target recycling, which in turn requires a plurality of probe complexes 18 and docking strands 20 capable of interacting with target 22.

Accordingly, device 100 may comprise a first plurality of probe complexes, each having a probe nucleic acid strand and a displacement nucleic acid strand hybridized thereto, the plurality of probe strands being identical and the plurality of displacement strands being identical, and a first plurality of docking nucleic acid strands, the plurality of docking strands being identical to one another. Such a plurality facilitates signal amplification by (and thus detection of) a single species of target 22 (or genus of targets 22 commonly possessing regions 22b and 22c).

Device 100 may include at least 10 probe complexes 18, at least 50 probe complexes 18, at least 100 probe complexes 18, at least 1000 probe complexes 18, even as many as 10,000, 50,000, or 100,000 probe complexes 18. Probe complexes 18 may be disposed on substrate 10 of device 100 at a density of $1/\mu m^2–10^{11}/\mu m^2$.

Device 100 may also include at least a second plurality of probe complexes and a second plurality of docking strands, in which the displacement strands of the second plurality are respectively identical to one another but different from the displacement strands of the first plurality; in which the probe strands of the second plurality are respectively identical to one another but different from those of the first plurality; and in which the docking strands are respectively identical to one another but different from those of the first plurality.

Such additional pluralities of probe complexes (with corresponding pluralities of docking strands) permit concurrent, multiplexed, amplification of signal by (and thus detection of) additional species of target 22.

Each of the pluralities of probe complexes 18 may be distinctly labeled. For example, in an illustrative device of the present invention, each of the distinct species of probe strand 14 may be labeled with a distinct fluorophore, the distinct fluorophores having optically distinguishable excitation and/or emission spectra.

Device 100 may include as few as 1, 5, or 10 distinct species of probe complex and corresponding docking strand, each present as a plurality thereof. Device 100 may include as many as 50, 100, 1,000, 5,000, 10,000, 100,000 even 500,000 distinct species of probe complex and docking strand, each plurally present in the device.

As shown in FIG. 3A, the device and method of the present invention cause target nucleic acid 22 to act as a catalyst in the transfer of probe 14 from its initial location at the site of attachment of displacement strand 12 to the site of attachment of docking strand 20. The signal resulting from such transfer is thus catalytically amplified. The extent of signal amplification depends upon the amount of substrate, i.e. probe complexes 18 and docking strands 20 of appropriate sequence, the time required for a single reaction cycle, and the elapsed time prior to detection (number of reaction cycles).

The devices and methods of the present invention may be used to amplify the signal by at least two-fold, 3-fold, 4-fold, even at least five-fold, 10-fold, 50-fold, 100-fold, 1000-fold, and even as much as 10,000-fold to 100,000 fold or more over the signal obtainable in an assay in which a probe with regions identical to regions 14b' and 14c' hybridizes to single-stranded target 22 without strand displacement. The reaction may be carried out under conditions in which the signal is amplified by a factor of $10^6$, $10^7$, even $10^8$, $10^9$, or as much as $10^{10}$-fold.

The devices and signal amplification methods of the present invention may be used to facilitate detection of nucleic acid targets in samples suspected of containing the target nucleic acid.

Target nucleic acid may be detected in a fluid sample by contacting the sample to device 100, wherein the first and second regions of the probe strands of the device (regions 14b' and 14c', respectively) are substantially complementary to the target, and the first, second and third regions of the probe strand (regions 14b', 14c' and 14d', respectively) are substantially complementary to the docking strand. Target nucleic acid present in the fluid sample catalyzes transfer of the probe strand from the immobilized displacement strand to the spatially segregated, separately addressable, immobilized docking strand.

Target may then be detected as either or both of a diminution of probe concentration at its original address (the site of attachment of displacement strand 12) or increase in probe concentration at the final address (the site of attachment of docking strand 20).

When probe 14 is labeled, target may be detected by detecting either or both of loss of signal at the original probe address or gain of signal at the final probe address. Detecting both the loss of signal at the original address and gain of signal at the final address may be used to increase the signal:noise ratio or to increase sensitivity of the assay.

Detection may be performed continuously, monitoring either or both of the decrease in signal at the displacement strand address or increase in signal at the docking strand address, or may be performed discretely at one or more desired times during the reaction or after its completion.

In other embodiments of the detection methods of the present invention, after target-mediated catalytic transfer of probe strands to the docking strand address, the immobilized docking strands 20 and docking complexes 26 may be separated from the fluid medium before detection. Such inhomogeneous phase assays may have advantages when labeled probe strands provide an unacceptable level of background signal.

Target nucleic acid may be any naturally occurring nucleic acid, such as DNA or RNA, or may be a nucleic acid derived therefrom, such as cDNA. Target may be single-stranded or double-stranded. When double-stranded, target is typically first denatured, as by application of heat or base such as NaOH.

Sample is contacted to device 100 under conditions suitable for the successive strand displacement reactions shown in FIGS. 2A and 2B.

Such conditions are well known in the art, and may readily and usefully be adapted from conditions established for standard hybridization reactions on analogous substrates.

For example, when substrate 10 is one used in microarray hybridizations, such as a glass slide, hybridization conditions may readily and usefully be adapted from microarray hybridization conditions. For example, standard high stringency microarray conditions for spotted cDNA microarrays may be 50% formamide, 5×SSC, 0.2 $\mu g/\mu l$ poly(dA), and 0.5% SDS at 42° C., followed by successive washes of the microarray in 1×SSC, 0.2% SDS at 55° C. for 5 minutes, and then 0.1×SSC, 0.2% SDS, at 55° C. for 20 minutes. Lower stringency conditions may usefully be the same as the high stringency conditions but with reduction in temperature for hybridization and washing, e.g. to room temperature (approximately 25° C.).

Hybridization may be conducted in the presence of hybridization enhancers, such as cetyltrimethylammonium bromide (CTAB), volume excluders, and nonspecific competitor nucleic acids, and at temperatures ranging from 20° C.–80° C., as is well known in the art.

Further adjustments in hybridization reaction conditions are well within the skill in the art.

The methods of the present invention provide a variety of advantages over other methods for amplifying signal and detecting a target nucleic acid. These advantages render the methods of the present invention well suited for field use, as in environmental detection and monitoring, and in point of care clinical use, including home use.

By effecting a substantial amplification in hybridization signal, the device and methods of the present invention may obviate the need for physical amplification of target prior to detection, as by polymerase chain reaction (PCR), nucleic acid sequence-based amplification (NASBA), self-sustained sequence recognition (3SR), ligase chain reaction (LCR), transcription-mediated amplification (TMA), rolling circle amplification (RCA), or strand displacement amplification (SDA).

By obviating the need for physical amplification of target, the present invention reduces the number of steps the user must perform before detection is effected, reducing hands-on assay time, manipulations that may introduce error, and opportunities for sample loss, and also obviates the need for the user to obtain oligonucleotide primers.

In addition, by obviating the need for physical amplification of target, the present invention also eliminates the problem of nonspecific target amplification that attends such enzymatic methods, a problem even when physical amplification is performed using proofreading enzymes, such polymerases having 3'–5' exonuclease activity.

Because the methods of the present invention may be practiced at a single reaction temperature, the device and methods of the present invention obviate the need for thermocycling, and thus the need for apparatus capable of performing such cycling. The isothermal nature of the present reaction may be particularly advantageous when detection is made electrochemically.

The methods of the present invention further obviate the need to label target nucleic acids, further reducing the number of manipulations required by the user.

In a variety of embodiments of the methods of the present invention, no separation of components is needed before detection, providing a homogeneous phase assay. Homogeneous phase assays are particularly well suited for field use, particularly by individuals lacking extensive training in laboratory arts.

The spatial component of the signal in the methods of the present invention provides further advantages.

For example, the transfer of probe from a first location to a second location may be used to distinguish spurious signals from true analyte-specific signals. Because true analyte-specific signals in the methods of the present invention necessarily couple the diminution of signal at a first address to an increase of signal at a second address, measuring both signals permits such signals to be distinguished from background, increasing the signal:noise ratio.

Alternatively, the spatial component of the signal may be exploited, by summing the absolute value of the signal changes at the two locations, to increase sensitivity of the assay.

Another advantage of the device and methods of the present invention is that the signal is a characteristic of the engineered probe strand, not of a labeled biological target, permitting the probe strand to be engineered to give an optimal, and characteristic, signal. For example, if electrochemical detection is employed, probe strand 14 may be engineered to provide a characteristic signal at a predetermined redox potential.

Analogously, probe strand 14, displacement strand 12, and docking strand 20 may readily be engineered to provide optimal reaction kinetics. For example, where a plurality of different probe complexes 18 (with correspondingly different docking strands 20) are used concurrently to detect a plurality of target species 22, the nucleic acids of device 100 may be engineered to permit optimal strand displacement with a single, common, set of hybridization conditions, facilitating multiplex analysis.

In addition, strand displacement reactions provide high specificity and selectivity. As set forth in detail in commonly owned U.S. patent application Ser. No. 10/178,682, filed Jun. 20, 2002, incorporated herein by reference in its entirety, the use of strand displacement complexes permits the selectivity of nucleic acid probes for polymorphic variants of their cognate targets to be adjusted, or "tuned", without compromising target specificity.

To effect such selectivity, probe strand 14 is duplexed within probe complex 18 across at least one region (region 12b') as to which target selectivity is desired to be tuned. Within the complex, probe strand 14 further has at least one region (region 12c') that is not duplexed by displacement strand 12, and is complementary to target 22 but as to which target selectivity is not desired to be tuned.

The relative lengths and positions of these two probe regions within probe complex 18 serve to adjust the proportional effect of a mismatch on the overall free energy change of the displacement reaction, and thus tunes the selectivity of the probe for polymorphic variants of the target.

Probe selectivity may be tuned to distinguish target variants that differ in sequence by as few as two nucleotides, and even by as few as one nucleotide.

The ability to tune the selectivity of longer probes for polymorphic variants of the probe's cognate target can be exploited to improve methods of detecting polymorphic variants of a target, including single nucleotide polymorphisms (SNPs).

In the methods of the present invention, the specificity and selectivity of strand displacement is independently effected with each reaction cycle, in contrast to physical target amplification techniques, such as PCR, in which mispriming in an early cycle provides template that is further amplified in successive cycles.

As a result, in the methods of the present invention signal is particularly amplified for the desired target, increasing the specificity of the assay.

The methods of the present invention may usefully be practiced using nanoscale devices, thus reducing the time required for diffusion of probe strand 14 to docking strand 20.

In addition, the movement of probe strand 14 may be further facilitated by bulk fluid flow, as may be imposed, e.g., by centripetal forces, by electrical fields, by electroosmosis, and by other microfluidic techniques. International patent publications WO 00/79285, WO 00/78455, WO 00/69560, and WO 98/53311, incorporated herein by reference in their entireties, describe devices and methods for using centripetal acceleration to drive fluid movement in a microfluidics system; international patent applications numbers WO 01/47638 and WO 01/46465, incorporated herein by reference in their entireties, describe rotatable discs having integrated microfluidics.

In another aspect, the present invention provides kits for amplifying the signal from hybridization of a nucleic acid probe to its cognate target.

In an illustrative embodiment, a kit of the present invention comprises a device, the device comprising: (i) at least one substrate; (ii) a first plurality of identical displacement nucleic acid strands; and (iii) a first plurality of identical docking nucleic acid strands. The displacement strands and the docking strands are immobilized to one of the at least one substrates, the immobilized displacement strands and the immobilized docking strands being spatially segregated from one another, separately addressable, and fluidly communicating upon contact of the device with fluid solvent.

The kit further comprises a composition comprising probe nucleic acid strands suitable for completion of the device. Accordingly, the probe nucleic strands have at least three regions: a first region that is substantially complementary to a region of each of the displacement strand, the cognate target, and the docking strand; a second region that is substantially complementary to a region of each of the cognate target and the docking strand, but not substantially complementary to a region of the displacement strand; and a third region that is substantially complementary to a region of the docking strand, but not substantially complementary to a region of either of the displacement strand or the cognate target.

The user desiring to amplify the signal from a nucleic acid hybridization reaction between probe and cognate target hybridizes the probe to the displacement strands of the device, taking care not to apply the probes to the docking strands of the device, and then performs the assay by contacting a fluid sample containing, or suspected to contain, the cognate target to the device so completed.

The probe strands of the composition may be detectably labeled, or the kit may further comprise reagents for detectably labeling the probe strands of the composition.

The kit may additionally comprise a control composition, the control composition comprising target nucleic acids capable of catalyzing transfer of the probes from the displacement strands of the device to the docking strands of the device.

All patents, patent publications, and other published references mentioned herein are hereby incorporated by reference in their entireties as if each had been individually and specifically incorporated by reference herein.

Although illustrative embodiments of the present invention are described above, it will be evident to one skilled in the art that various changes and modifications may be made without departing from the spirit and scope of the invention. Many examples of such modifications have been given through the foregoing specification. It is intended that the appended claims cover all such changes and modifications that fall within the true spirit and scope of the invention.

What is claimed is:

1. A device for nonenzymatically amplifying the signal from a hybridization reaction between at least a first nucleic acid probe and its cognate nucleic acid target present in fluid solvent, the device comprising:
   at least one substrate;
   a first plurality of probe complexes, each having a probe nucleic acid strand and a displacement nucleic acid strand hybridized thereto, the plurality of probe strands being identical and the plurality of displacement strands being identical; and
   a first plurality of identical docking nucleic acid strands, wherein the displacement strands and the docking strands are immobilized to one of said at least one substrates, said immobilized displacement strands and said immobilized docking strands being spatially segregated from one another, separately addressable, and fluidly communicating upon contact of said device with fluid solvent,
   wherein the probe strand of said probe complexes has at least three regions,
   a first region that is substantially complementary to a region of each of the displacement strand, the target, and the docking strand;

a second region that is substantially complementary to a region of each of the target and the docking strand, but not substantially complementary to a region of the displacement strand; and a third region that is substantially complementary to a region of the docking strand, but not substantially complementary to a region of either of the displacement strand or the target, whereby contact of target to said device is capable of catalyzing transfer of probe strands from the displacement strands to the spatially segregated, separately addressable docking strands, the transfer of said probe generating a detectable signal.

2. The device of claim 1, wherein said at least one substrate is a unitary substrate.

3. The device of claim 2, wherein said unitary substrate has a substantially planar surface to which said displacement strands and docking strands are segregably attached.

4. The device of claim 2, wherein said unitary substrate is at least one internal wall of a capillary, channel, or chamber formed in said device.

5. The device of either of claim 3 or 4, wherein said substrate comprises glass, silicon, or plastic.

6. The device of claim 1, wherein said at least one substrate is an array of electrodes.

7. The device of claim 1, wherein said probe strands further comprise a signaling moiety.

8. The device of claim 7, wherein said signaling moiety is optically detectable.

9. The device of claim 8, wherein said signaling moiety is a fluorophore.

10. The device of claim 7, wherein said signaling moiety is electrochemically detectable.

11. The device of claim 10, wherein said signaling moiety is a polyguanidine polymer.

12. The device of claim 10, wherein said signaling moiety includes a ferrocenyl group.

13. The device of claim 7, wherein said signaling moiety is radioactive.

14. The device of claim 1, wherein either or both of the second and third regions of said probe strands is independently 2–14 nucleotides in length.

15. The device of claim 14, wherein either or both of the second and third regions of said probe strands is independently 2–10 nucleotides in length.

16. The device of claim 15, wherein either or both of the second and third regions of said probe strands is independently 2–6 nucleotides in length.

17. The device of claim 1, wherein any or all of said probe strands, said displacement strands, and said docking strands are peptide nucleic acids.

18. The device of claim 1, wherein any or all of said probe strands, said displacement strands, and said docking strands include locked nucleic acid analogues.

19. The device of claim 1, further comprising a second plurality of probe complexes and a second plurality of docking strands, wherein the displacement strands, probe strands, and docking strands of said second pluralities are respectively identical thereamong but differ from those of said first plurality, and said probe strand first and second regions are substantially complementary to a second nucleic acid target.

20. The device of claim 19, wherein said second plurality of probe strands are distinguishably labeled from said first plurality of probe strands.

21. The device of claim 20, wherein said first and second plurality of probe strands are respectively labeled with a first and second fluorophore, said first and second fluorophore having optically distinguishable excitation or emission spectra.

22. A method of detecting a hybridization reaction between a nucleic acid probe and its cognate nucleic acid target with a catalytically amplified signal, the method comprising:

contacting the target in a fluid solvent to a device according to claim 1, wherein the first and second regions of the probe strands of said device are substantially complementary to said target and said target catalyzes transfer of the probe strand from the immobilized displacement strand to the spatially segregated, spatially addressable, immobilized docking strand, the transfer of said probe generating a detectable signal; and then detecting the detectable signal.

23. The method of claim 22, wherein said signal is detected as a diminution of signal at the displacement strand address.

24. The method of claim 22, wherein said signal is detected as an increase of signal at the docking strand address.

25. The method of claim 22, wherein said signal is detected both as a diminution of signal at the displacement strand address and increase of signal at the docking strand address.

26. The method of claim 22, wherein the signal is optically detectable.

27. The method of claim 26, wherein the signal is fluorescent.

28. The method of claim 22, wherein the signal is electrochemically detectable.

29. The method of claim 22, wherein the signal is mass spectrally detectable.

30. The method of claim 22, further comprising the step, after contacting and before detecting, of:

separating the immobilized docking strands from said fluid solvent.

31. A kit for nonenzymatically amplifying the signal from a hybridization reaction between at least a first nucleic acid probe and its cognate nucleic acid target present in fluid solvent, comprising:

a device, the device comprising:
at least one substrate;
a first plurality of identical displacement nucleic acid strands; and
a first plurality of identical docking nucleic acid strands,
wherein the displacement strands and the docking strands are immobilized to one of said at least one substrates, said immobilized displacement strands and said immobilized docking strands being spatially segregated from one another, separately addressable, and fluidly communicating upon contact of said device with fluid solvent; and a composition comprising probe nucleic acid strands, the probe nucleic strands having at least three regions, a first region that is substantially complementary to a region of each of the displacement strand, the target, and the docking strand;

a second region that is substantially complementary to a region of each of the target and the docking strand, but not substantially complementary to a region of the displacement strand; and a third region that is substantially complementary to a region of the docking strand, but not substantially complementary to a region of either of the displacement strand or the target.

32. The kit of claim 31, wherein said probe strands are detectably labeled.

33. The kit of claim 31, further comprising reagents for detectably labeling the probe strands of said composition.

34. The kit of claim 31, further comprising a control composition, said composition comprising target nucleic acids capable of catalyzing transfer of said probes from said displacement strands to said docking strands.

* * * * *